United States Patent
Kim

(10) Patent No.: US 11,406,362 B2
(45) Date of Patent: Aug. 9, 2022

(54) PROVIDING USER INTERFACE IN ULTRASOUND SYSTEM

(71) Applicant: SAMSUNG MEDISON CO., LTD., Gangwon-do (KR)

(72) Inventor: Hyoung Jin Kim, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 1039 days.

(21) Appl. No.: 15/467,882

(22) Filed: Mar. 23, 2017

(65) Prior Publication Data

US 2017/0188998 A1 Jul. 6, 2017

Related U.S. Application Data

(63) Continuation of application No. 13/730,501, filed on Dec. 28, 2012, now abandoned.

(30) Foreign Application Priority Data

Dec. 28, 2011 (KR) .................... 10-2011-0144476

(51) Int. Cl.
*A61B 8/08* (2006.01)
*A61B 8/13* (2006.01)
(Continued)

(52) U.S. Cl.
CPC .............. *A61B 8/488* (2013.01); *A61B 8/06* (2013.01); *A61B 8/08* (2013.01); *A61B 8/13* (2013.01); *A61B 8/463* (2013.01); *A61B 8/465* (2013.01); *A61B 8/469* (2013.01); *G01S 7/52063* (2013.01); *G01S 7/52071* (2013.01);
(Continued)

(58) Field of Classification Search
None
See application file for complete search history.

(56) References Cited

U.S. PATENT DOCUMENTS 4,768,515 A    9/1988  Namekawa
5,123,417 A * 6/1992  Walker ................ G01S 15/8979
                                        348/163

(Continued)

FOREIGN PATENT DOCUMENTS

JP     H09-75341 A    3/1997
JP     H10-14917 A    1/1998

(Continued)

OTHER PUBLICATIONS

European Communication dated Jan. 14, 2019 issued in European Patent Application No. 12199541.9.

(Continued)

*Primary Examiner* — Jonathan Cwern
(74) *Attorney, Agent, or Firm* — Morgan, Lewis & Bockius LLP

(57) ABSTRACT

There are provided embodiments for providing a user interface for performing a filtering process upon a vector Doppler image. In one embodiment, by way of non-limiting example, an ultrasound system comprises: a processing unit configured to form vector information of a target object based on ultrasound data corresponding to the target object and form a user interface for performing the filtering process upon the vector Doppler image based on the vector information.

10 Claims, 19 Drawing Sheets

(51) Int. Cl.
*G01S 15/89* (2006.01)
*A61B 8/00* (2006.01)
*A61B 8/06* (2006.01)
*G10K 11/34* (2006.01)
*G01S 7/52* (2006.01)
*G06V 10/40* (2022.01)

(52) U.S. Cl.
CPC ...... *G01S 7/52073* (2013.01); *G01S 7/52095* (2013.01); *G01S 15/8984* (2013.01); *G01S 15/8988* (2013.01); *G06V 10/40* (2022.01); *G10K 11/341* (2013.01)

(56) References Cited

U.S. PATENT DOCUMENTS

| | | | |
|---|---|---|---|
| 5,622,174 A * | 4/1997 | Yamazaki | A61B 8/463 600/441 |
| 5,910,119 A | 6/1999 | Lin | |
| 6,176,828 B1 | 1/2001 | Becker et al. | |
| 7,621,872 B2 | 11/2009 | Hyun | |
| 7,648,461 B2 * | 1/2010 | Thiele | A61B 8/06 600/437 |
| 2002/0173721 A1 | 11/2002 | Grunwald et al. | |
| 2003/0013959 A1 | 1/2003 | Grunwald et al. | |
| 2003/0149366 A1 | 8/2003 | Stringer et al. | |
| 2007/0083099 A1 | 4/2007 | Henderson et al. | |
| 2008/0091107 A1 | 4/2008 | Kim | |
| 2008/0167557 A1 | 7/2008 | Kozai | |
| 2009/0030321 A1 | 1/2009 | Baba et al. | |
| 2010/0069757 A1 | 3/2010 | Yoshikawa et al. | |
| 2010/0125196 A1 | 5/2010 | Park et al. | |
| 2010/0145195 A1 * | 6/2010 | Hyun | G01S 7/52082 600/437 |
| 2010/0298701 A1 | 11/2010 | Shin | |
| 2010/0305440 A1 | 12/2010 | Lee et al. | |
| 2010/0321324 A1 | 12/2010 | Fukai et al. | |
| 2011/0196237 A1 | 8/2011 | Pelissier et al. | |
| 2011/0246876 A1 * | 10/2011 | Chutani | A61B 8/4427 715/702 |
| 2014/0098049 A1 * | 4/2014 | Koch | A61B 8/467 345/173 |

FOREIGN PATENT DOCUMENTS

| | | |
|---|---|---|
| JP | 11-299785 A | 11/1999 |
| JP | 2000-139914 A | 5/2000 |
| JP | 2002-017685 A | 1/2002 |
| JP | 2006-055493 A | 3/2006 |
| JP | 2009-005829 A | 1/2009 |
| JP | 2009-285244 A | 12/2009 |
| KR | 10-0825054 B1 | 4/2008 |
| KR | 10-0951595 B1 | 4/2010 |
| KR | 10-2010-0055092 A | 5/2010 |
| KR | 10-2010-0110893 A | 10/2010 |
| KR | 10-2010-0125966 A | 12/2010 |
| KR | 10-2010-0129681 A | 12/2010 |

OTHER PUBLICATIONS

N. Vera, et al., "Visualization of Complex Flow Fields, with Application To The Interpretation of Colour Flow Doppler Images," Ultrasound in Med. & Biol., vol. 18, No. 1, pp. 1992, pp. 1-9.

Non-Final Rejection issued in U.S. Appl. No. 13/730,501, dated Nov. 24, 2014.

Final Rejection issued in U.S. Appl. No. 13/730,501, dated Feb. 23, 2015.

Non-Final Rejection issued in U.S. Appl. No. 13/730,501, dated Sep. 18, 2015.

Final Rejection issued in U.S. Appl. No. 13/730,501, dated Jan. 21, 2016.

Non-Final Rejection issued in U.S. Appl. No. 13/730,501, dated Jun. 20, 2016.

Non-Final Rejection issued in U.S. Appl. No. 13/730,501, dated Dec. 23, 2016.

Korean Office Action issued in Korean Application No. 10-2011-144476 dated Mar. 14, 2014, w/English abstract.

Korean Office Action, w/ English translation thereof, issued in Korean Patent Application No. KR 10-2011-0144476 dated Nov. 28, 2013.

Extended European Search Report issued in European Patent Application No. EP 12199541.9 dated May 6, 2013.

Korean Office Action issued in Korean Patent Application No. KR 10-2011-0144476 dated May 15, 2013.

* cited by examiner

FIG. 7
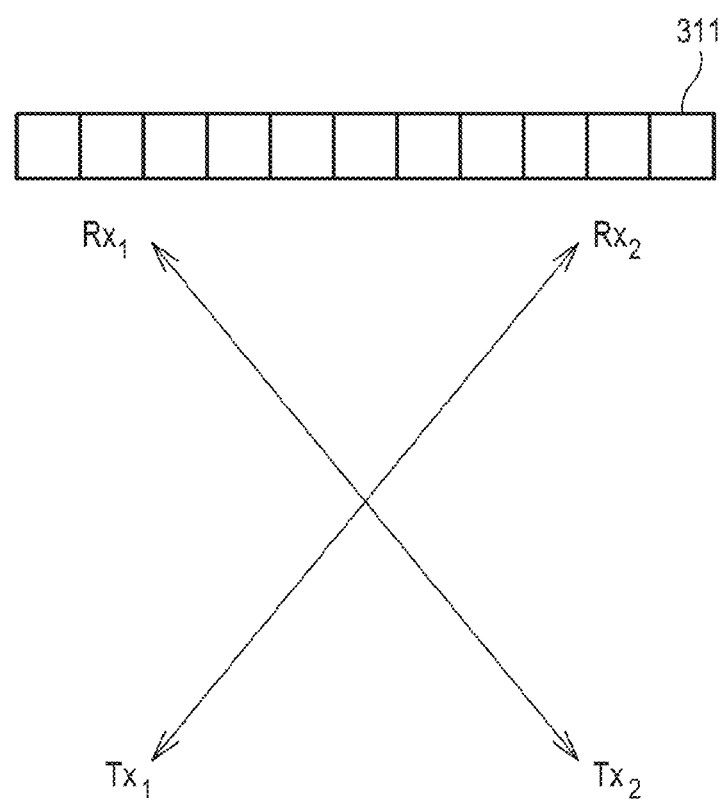
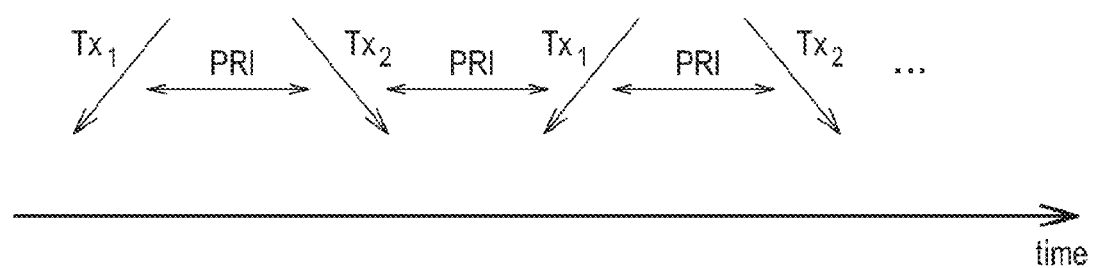

FIG. 8

| $S_{1,t}$ | $S_{2,t}$ | $S_{3,t}$ | $S_{4,t}$ | $S_{5,t}$ | $S_{6,t}$ | $S_{7,t}$ | $S_{8,t}$ | $S_{9,t}$ | $S_{10,t}$ | $S_{11,t}$ | $\cdots$ | $S_{p,t}$ |
|---|---|---|---|---|---|---|---|---|---|---|---|---|
| $\vdots$ | $\vdots$ | $\vdots$ | $\vdots$ | $\vdots$ | $\vdots$ | $\vdots$ | $\vdots$ | $\vdots$ | $\vdots$ | $\vdots$ | $\vdots$ | $\vdots$ |
| $S_{1,6}$ | $S_{2,6}$ | $S_{3,6}$ | $S_{4,6}$ | $S_{5,6}$ | $S_{6,6}$ | $S_{7,6}$ | $S_{8,6}$ | $S_{9,6}$ | $S_{10,6}$ | $S_{11,6}$ | $\cdots$ | $S_{p,6}$ |
| $S_{1,5}$ | $S_{2,5}$ | $S_{3,5}$ | $S_{4,5}$ | $S_{5,5}$ | $S_{6,5}$ | $S_{7,5}$ | $S_{8,5}$ | $S_{9,5}$ | $S_{10,5}$ | $S_{11,5}$ | $\cdots$ | $S_{p,5}$ |
| $S_{1,4}$ | $S_{2,4}$ | $S_{3,4}$ | $S_{4,4}$ | $S_{5,4}$ | $S_{6,4}$ | $S_{7,4}$ | $S_{8,4}$ | $S_{9,4}$ | $S_{10,4}$ | $S_{11,4}$ | $\cdots$ | $S_{p,4}$ |
| $S_{1,3}$ | $S_{2,3}$ | $S_{3,3}$ | $S_{4,3}$ | $S_{5,3}$ | $S_{6,3}$ | $S_{7,3}$ | $S_{8,3}$ | $S_{9,3}$ | $S_{10,3}$ | $S_{11,3}$ | $\cdots$ | $S_{p,3}$ |
| $S_{1,2}$ | $S_{2,2}$ | $S_{3,2}$ | $S_{4,2}$ | $S_{5,2}$ | $S_{6,2}$ | $S_{7,2}$ | $S_{8,2}$ | $S_{9,2}$ | $S_{10,2}$ | $S_{11,2}$ | $\cdots$ | $S_{p,2}$ |
| $S_{1,1}$ | $S_{2,1}$ | $S_{3,1}$ | $S_{4,1}$ | $S_{5,1}$ | $S_{6,1}$ | $S_{7,1}$ | $S_{8,1}$ | $S_{9,1}$ | $S_{10,1}$ | $S_{11,1}$ | $\cdots$ | $S_{p,1}$ |
| $CH_1$ | $CH_2$ | $CH_3$ | $CH_4$ | $CH_5$ | $CH_6$ | $CH_7$ | $CH_8$ | $CH_9$ | $CH_{10}$ | $CH_{11}$ | $\cdots$ | $CH_p$ |

| $P_{1,1}$ | $P_{1,2}$ | $P_{1,3}$ | $P_{1,4}$ | $P_{1,5}$ | $P_{1,6}$ | $P_{1,7}$ | $P_{1,8}$ | $P_{1,9}$ | $\cdots$ | $P_{1,N}$ |
|---|---|---|---|---|---|---|---|---|---|---|
| $P_{2,1}$ | $P_{2,2}$ | $P_{2,3}$ | $P_{2,4}$ | $P_{2,5}$ | $P_{2,6}$ | $P_{2,7}$ | $P_{2,8}$ | $P_{2,9}$ | $\cdots$ | $P_{2,N}$ |
| $P_{3,1}$ | $P_{3,2}$ | $P_{3,3}$ | $P_{3,4}$ | $P_{3,5}$ | $P_{3,6}$ | $P_{3,7}$ | $P_{3,8}$ | $P_{3,9}$ | $\cdots$ | $P_{3,N}$ |
| $P_{4,1}$ | $P_{4,2}$ | $P_{4,3}$ | $P_{4,4}$ | $P_{4,5}$ | $P_{4,6}$ | $P_{4,7}$ | $P_{4,8}$ | $P_{4,9}$ | $\cdots$ | $P_{4,N}$ |
| $P_{5,1}$ | $P_{5,2}$ | $P_{5,3}$ | $P_{5,4}$ | $P_{5,5}$ | $P_{5,6}$ | $P_{5,7}$ | $P_{5,8}$ | $P_{5,9}$ | $\cdots$ | $P_{5,N}$ |
| $P_{6,1}$ | $P_{6,2}$ | $P_{6,3}$ | $P_{6,4}$ | $P_{6,5}$ | $P_{6,6}$ | $P_{6,7}$ | $P_{6,8}$ | $P_{6,9}$ | $\cdots$ | $P_{6,N}$ |
| $P_{7,1}$ | $P_{7,2}$ | $P_{7,3}$ | $P_{7,4}$ | $P_{7,5}$ | $P_{7,6}$ | $P_{7,7}$ | $P_{7,8}$ | $P_{7,9}$ | $\cdots$ | $P_{7,N}$ |
| $\vdots$ | $\vdots$ | $\vdots$ | $\vdots$ | $\vdots$ | $\vdots$ | $\vdots$ | $\vdots$ | $\vdots$ | $\vdots$ | $\vdots$ |
| $P_{M,1}$ | $P_{M,2}$ | $P_{M,3}$ | $P_{M,4}$ | $P_{M,5}$ | $P_{M,6}$ | $P_{M,7}$ | $P_{M,8}$ | $P_{M,9}$ | $\cdots$ | $P_{M,N}$ |

FIG. 13
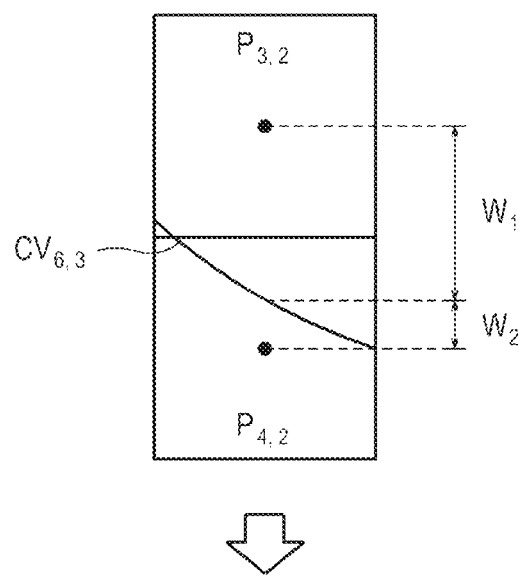
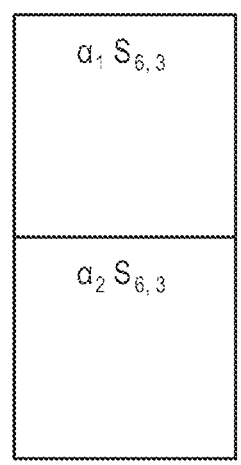

FIG. 14

FIG. 16
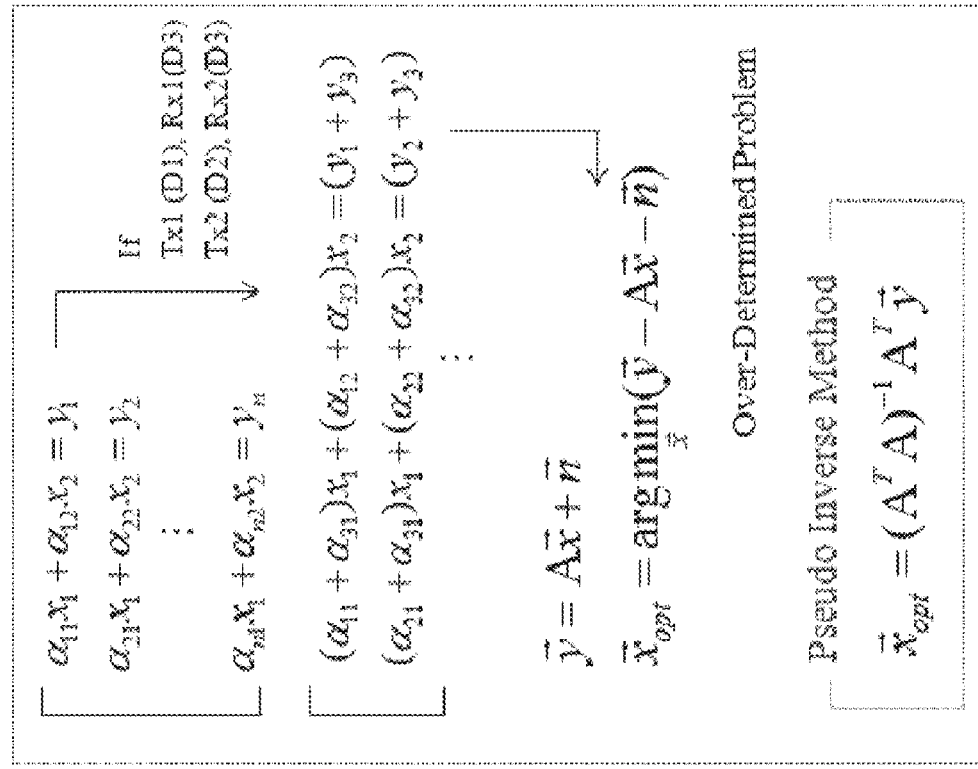
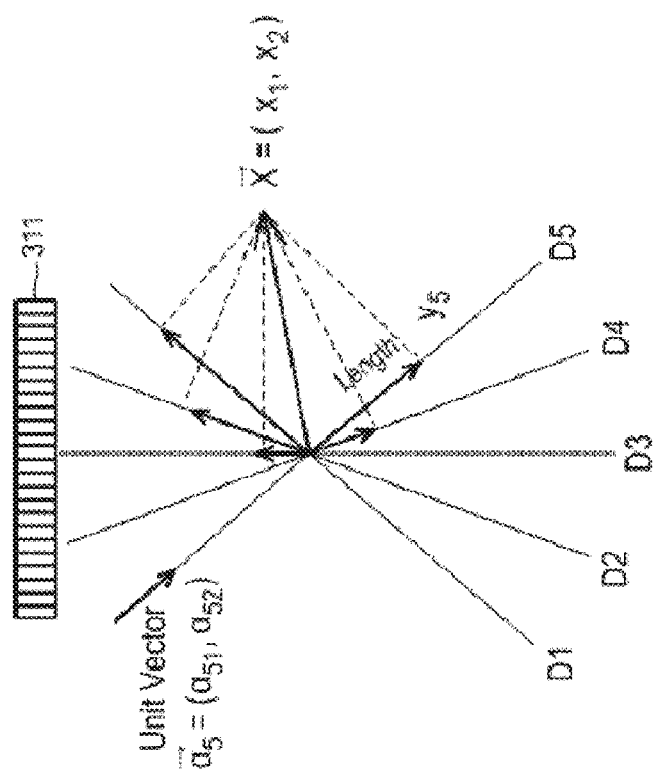

PROVIDING USER INTERFACE IN ULTRASOUND SYSTEM

CROSS-REFERENCE TO RELATED APPLICATIONS

The present application is a Continuation of U.S. patent application Ser. No. 13/730,501, filed on Dec. 28, 2012 which in turns claims priority from Korean Patent Application No. 10-2011-0144476 filed on Dec. 28, 2011, the entire subject matter of which are incorporated herein by reference.

TECHNICAL FIELD

The present disclosure generally relates to ultrasound systems, and more particularly to providing a user interface for performing a filtering process upon a vector Doppler image in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two-dimensional or three-dimensional ultrasound images of internal features of target objects (e.g., human organs).

The ultrasound system may provide ultrasound images of various modes including a brightness mode image representing reflection coefficients of ultrasound signals (i.e., ultrasound echo signals) reflected from a target object of a living body with a two-dimensional image, a Doppler mode image representing velocity of a moving target object with spectral Doppler by using a Doppler effect, a color Doppler mode image representing velocity of the moving target object with colors by using the Doppler effect, an elastic image representing mechanical characteristics of tissues before and after applying compression thereto and the like.

The ultrasound system may transmit the ultrasound signals to the living body and receive the ultrasound echo signals from the living body to form Doppler signals corresponding to a region of interest, which is set on the brightness mode image. The ultrasound system may further form the color Doppler mode image representing the velocity of the moving target object with colors based on the Doppler signals. In particular, the color Doppler image may represent the motion of the target object (e.g., blood flow) with the colors. The color Doppler image may be used to diagnose diseases of blood vessels, heart and the like. However, it is difficult to represent an accurate motion of the target object (e.g., blood flow) since the respective colors indicated by a motion value is a function of the velocity of the target object, which moves forward in a transmission direction of the ultrasound signals and moves backward in the transmission direction of the ultrasound signals.

To resolve this problem, a vector Doppler method capable of obtaining the velocity and direction of the blood flow is used. A cross beam-based method of the vector Doppler method may acquire velocity magnitude components from at least two different directions, and combine the velocity magnitude components to detect vector information having a two-dimensional or three-dimensional direction information and a magnitude information.

SUMMARY

There are provided embodiments for providing a user interface for performing a filtering process upon a vector Doppler image.

In one embodiment, by way of non-limiting example, an ultrasound system comprises: a processing unit configured to form vector information of a target object based on ultrasound data corresponding to the target object, and form a user interface for performing a filtering process upon a vector Doppler image based on the vector information.

In another embodiment, there is provided a method of providing a user interface, comprising: a) forming vector information of a target object based on ultrasound data corresponding to the target object; and b) forming a user interface for performing a filtering process upon a vector Doppler image based on the vector information.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIGS. 4 to 7 are schematic diagrams showing examples of transmission directions and reception directions.

FIG. 8 is a schematic diagram showing an example of sampling data and pixels of an ultrasound image.

FIGS. 9 to 12 are schematic diagrams showing examples of performing a reception beam-forming.

FIG. 13 is a schematic diagram showing an example of setting weights.

FIG. 14 is a schematic diagram showing an example of setting a sampling data set.

FIG. 16 is a schematic diagram showing an example of the transmission directions, the reception directions, the vector information and an over-determined problem.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
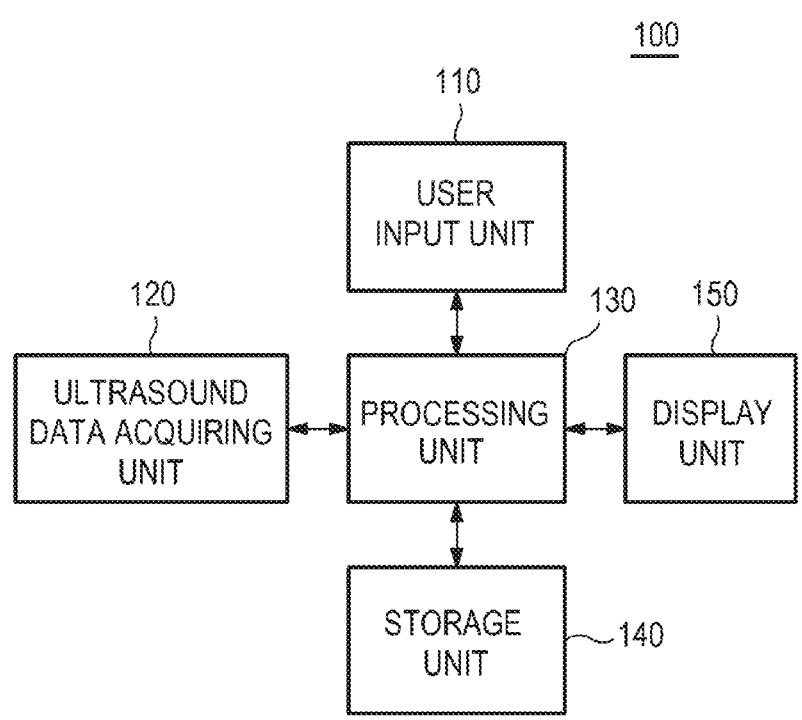
FIG. 1 is a block diagram showing an illustrative embodiment of an ultrasound system.

Referring to FIG. 1, an ultrasound system 100 in accordance with an illustrative embodiment is shown. As depicted therein, the ultrasound system 100 may include a user input unit 110.

Figure 2:
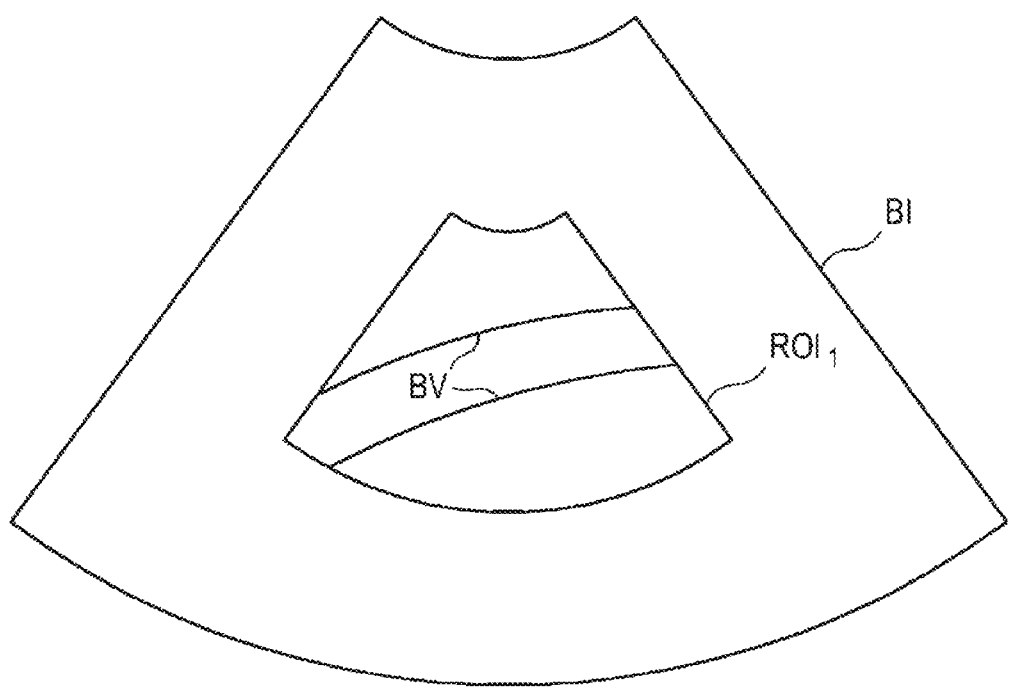
FIG. 2 is a schematic diagram showing an example of a brightness mode image and a first region of interest.

The user input unit 110 may be configured to receive input information from a user. In one embodiment, the input information may include first input information for setting a first region of interest $ROI_1$ on a brightness mode image BI, as shown in FIG. 2. The first region of interest $ROI_1$ may include a color box for obtaining a Doppler mode image. The Doppler mode image may include a vector Doppler image corresponding to motion (i.e., velocity and direction) of a target object. The input information may further include second input information for setting at least one region for representing only the motion of target in a specific direction on the vector Doppler image. However, it should be noted herein that the input information may not be limited thereto. In FIG. 2, the reference numeral BV represents a blood vessel. The user input unit 110 may include a control panel, a track ball, a touch screen, a keyboard, a mouse and the like.

The ultrasound system 100 may further include an ultrasound data acquiring unit 120. The ultrasound data acquiring unit 120 may be configured to transmit ultrasound signals to a living body. The living body may include the target object (e.g., blood flow, blood vessel, heart, etc.). The ultrasound data acquiring unit 120 may be further configured to receive ultrasound signals (i.e., ultrasound echo signals) from the living body to acquire ultrasound data corresponding to an ultrasound image.

Figure 3:
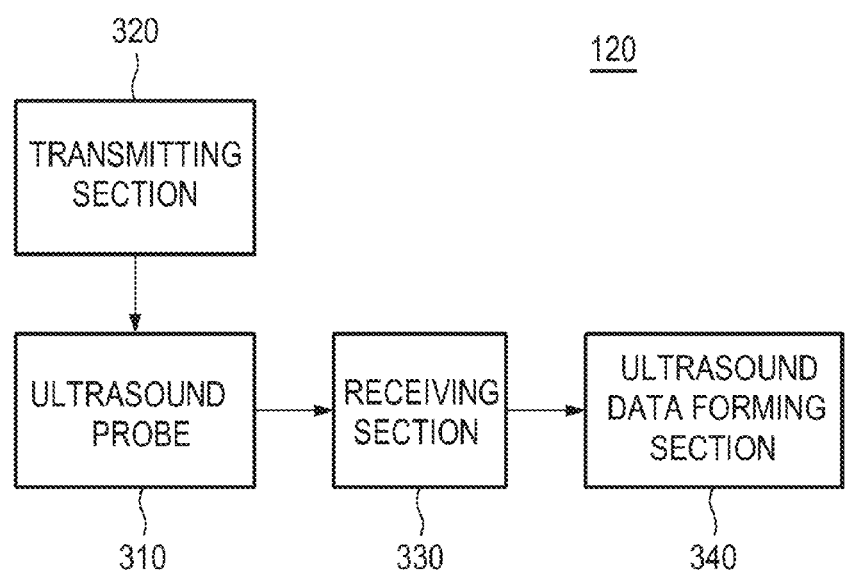
FIG. 3 is a block diagram showing an illustrative embodiment of an ultrasound data acquiring unit.

FIG. 3 is a block diagram showing an illustrative embodiment of the ultrasound data acquiring unit 120. Referring to FIG. 3, the ultrasound data acquiring unit 120 may include an ultrasound probe 310.

The ultrasound probe 310 may include a plurality of elements 311 (see FIG. 4) for reciprocally converting between ultrasound signals and electrical signals. The ultrasound probe 310 may be configured to transmit the ultrasound signals to the living body. The ultrasound signals transmitted from the ultrasound probe 310 may be plane wave signals that the ultrasound signals are not focused at a focusing point, or focused signals that the ultrasound signals are focused at the focusing point. However, it should be noted herein that the ultrasound signals may not be limited thereto. The ultrasound probe 310 may be further configured to receive the ultrasound echo signals from the living body to output electrical signals (hereinafter referred to as "reception signals"). The reception signals may be analog signals. The ultrasound probe 310 may include a convex probe, a linear probe and the like.

The ultrasound data acquiring unit 120 may further include a transmitting section 320. The transmitting section 320 may be configured to control the transmission of the ultrasound signals. The transmitting section 320 may be also configured to generate electrical signals (hereinafter referred to as "transmission signals") in consideration of the elements 311.

In one embodiment, the transmitting section 320 may be configured to generate transmission signals (hereinafter referred to as "brightness mode transmission signals") for obtaining the brightness mode image BI in consideration of the elements 311. Thus, the ultrasound probe 310 may be configured to convert the brightness mode transmission signals provided from the transmitting section 320 into the ultrasound signals, transmit the ultrasound signals to the living body, and receive the ultrasound echo signals from the living body to output reception signals (hereinafter referred to as "brightness mode reception signals").

The transmitting section 320 may be further configured to generate transmission signals (hereinafter referred to as "Doppler mode transmission signals") corresponding to an ensemble number in consideration of the elements 311 and at least one transmission direction of the ultrasound signals (i.e., transmission beam). Thus, the ultrasound probe 310 may be configured to convert the Doppler mode transmission signals provided from the transmitting section 320 into the ultrasound signals, transmit the ultrasound signals to the living body in the at least one transmission direction, and receive the ultrasound echo signals from the living body to output reception signals (hereinafter referred to as "Doppler mode reception signals"). The ensemble number may represent the number of transmitting and receiving the ultrasound signals to and from the living body.

Figure 4:
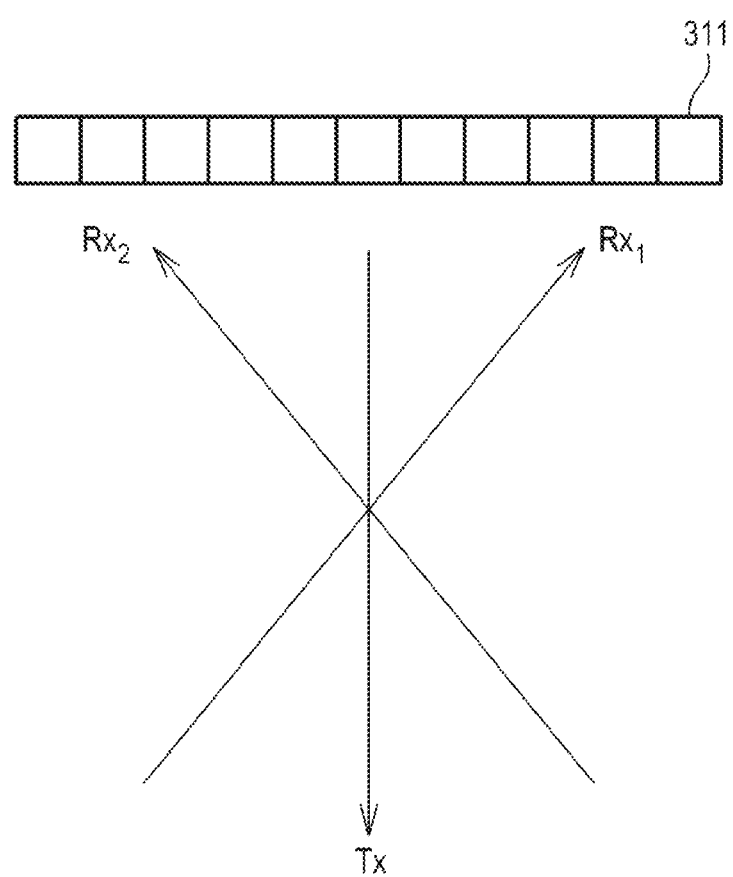

As one example, the transmitting section 320 may be configured to generate the Doppler mode transmission signals corresponding to the ensemble number in consideration of a transmission direction Tx and the elements 311, as shown in FIG. 4. The transmission direction may be one of a direction (i.e., 0 degree) perpendicular to a longitudinal direction of the elements 311 to a maximum steering direction of the transmission beam.

Figure 5:
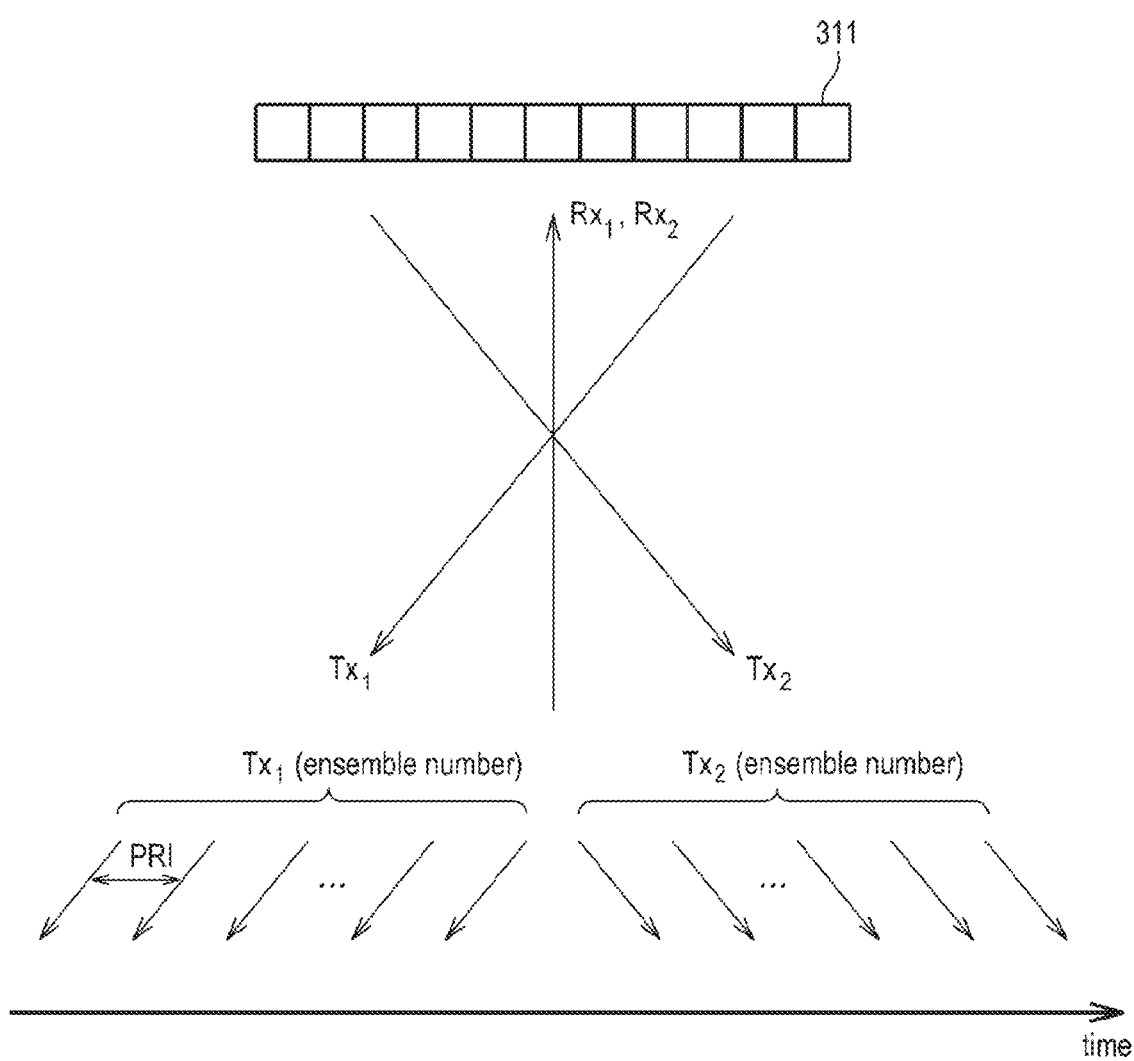

As another example, the transmitting section 320 may be configured to generate first Doppler mode transmission signals corresponding to the ensemble number in consideration of a first transmission direction $Tx_1$ and the elements 311, as shown in FIG. 5. Thus, the ultrasound probe 310 may be configured to convert the first Doppler mode transmission signals provided from the transmitting section 320 into the ultrasound signals, transmit the ultrasound signals to the living body in the first transmission direction $Tx_1$, and receive the ultrasound echo signals from the living body to output first Doppler mode reception signals. The transmitting section 320 may be further configured to generate second Doppler mode transmission signals corresponding to the ensemble number in consideration of a second transmission direction $Tx_2$ and the elements 311, as shown in FIG. 5. Thus, the ultrasound probe 310 may be configured to convert the second Doppler mode transmission signals provided from the transmitting section 320 into the ultrasound signals, transmit the ultrasound signals to the living body in the second transmission direction $Tx_2$, and receive the ultrasound echo signals from the living body to output second Doppler mode reception signals. In FIG. 5, the reference numeral PRI represents a pulse repeat interval.

In another embodiment, the transmitting section 320 may be configured to generate the brightness mode transmission signals for obtaining the brightness mode image BI in consideration of the elements 311. Thus, the ultrasound probe 310 may be configured to convert the brightness mode transmission signals provided from the transmitting section 320 into the ultrasound signals, transmit the ultrasound signals to the living body, and receive the ultrasound echo signals from the living body to output the brightness mode reception signals.

The transmitting section 320 may be further configured to generate the Doppler mode transmission signals corresponding to the ensemble number in consideration of the at least one transmission direction and the elements 311. Thus, the ultrasound probe 310 may be configured to convert the Doppler mode transmission signals provided from the transmitting section 320 into the ultrasound signals, transmit the ultrasound signals to the living body, and receive the ultrasound echo signals from the living body to output the Doppler mode reception signals. The ultrasound signals may be transmitted in an interleaved transmission scheme. The interleaved transmission scheme will be described below in detail.

Figure 6:
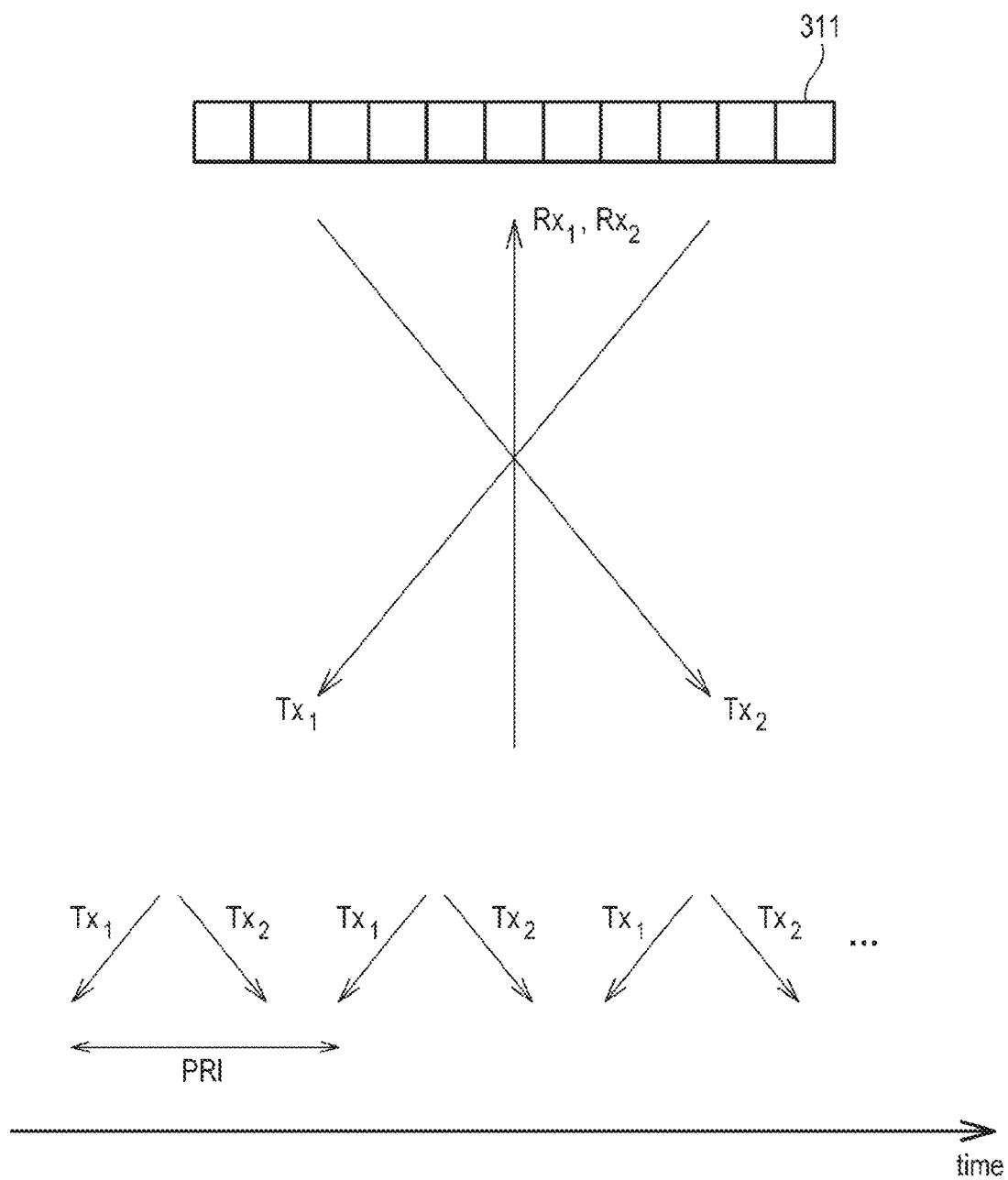

For example, the transmitting section 320 may be configured to generate the first Doppler mode transmission signals in consideration of the first transmission direction $Tx_1$ and the elements 311, as shown in FIG. 6. Thus, the ultrasound probe 310 may be configured to convert the first Doppler mode transmission signals provided from the transmitting section 320 into the ultrasound signals, and transmit the ultrasound signals to the living body in the first transmission direction $Tx_1$. The transmitting section 320 may be further configured to generate the second Doppler mode transmission signals in consideration of the second transmission direction $Tx_2$ and the elements 311, as shown in FIG. 6. Thus, the ultrasound probe 310 may be configured to convert the second Doppler mode transmission signals provided from the transmitting section 320 into the ultrasound signals, and transmit the ultrasound signals to the living body in the second transmission direction $Tx_2$. The ultrasound probe 310 may be further configured to receive the ultrasound echo signals (i.e., ultrasound echo signals corresponding to first Doppler mode transmission signals) from the living body to output the first Doppler mode reception signals. The ultrasound probe 310 may be further configured to receive the ultrasound echo signals (i.e., ultrasound echo signals corresponding to second Doppler mode transmission signals) from the living body to output the second Doppler mode reception signals.

Thereafter, the transmitting section 320 may be configured to generate the first Doppler mode transmission signals based on the pulse repeat interval, as shown in FIG. 6. Thus, the ultrasound probe 310 may be configured to convert the first Doppler mode transmission signals provided from the transmitting section 320 into the ultrasound signals, and transmit the ultrasound signals to the living body in the first transmission direction $Tx_1$. Then, the transmitting section 320 may be further configured to generate the second Doppler mode transmission signals based on the pulse repeat interval, as shown in FIG. 6. Accordingly, the ultrasound probe 310 may be configured to convert the second Doppler mode transmission signals provided from the transmitting section 320 into the ultrasound signals, and transmit the ultrasound signals to the living body in the second transmission direction $Tx_2$. The ultrasound probe 310 may be further configured to receive the ultrasound echo signals (i.e., ultrasound echo signals corresponding to first Doppler mode transmission signals) from the living body to output the first Doppler mode reception signals. The ultrasound probe 310 may be further configured to receive the ultrasound echo signals (i.e., ultrasound echo signals corresponding to second Doppler mode transmission signals) from the living body to output the second Doppler mode reception signals.

As described above, the transmitting section 320 may be configured to generate the first Doppler mode transmission signals and the second Doppler mode transmission signals corresponding to the ensemble number.

In yet another embodiment, the transmitting section 320 may be configured to generate the brightness mode transmission signals for obtaining the brightness mode image BI in consideration of the elements 311. Thus, the ultrasound probe 310 may be configured to convert the brightness mode transmission signals provided from the transmitting section 320 into the ultrasound signals, transmit the ultrasound signals to the living body, and receive the ultrasound echo signals from the living body to output the brightness mode reception signals.

The transmitting section 320 may be further configured to generate the Doppler mode transmission signals corresponding to the ensemble number in consideration of the at least one transmission direction and the elements 311. Thus, the ultrasound probe 310 may be configured to convert the Doppler mode transmission signals provided from the transmitting section 320 into the ultrasound signals, transmit the ultrasound signals to the living body in the at least one transmission direction, and receive the ultrasound echo signals from the living body to output the Doppler mode reception signals. The ultrasound signals may be transmitted according to the pulse repeat interval.

For example, the transmitting section 320 may be configured to generate the first Doppler mode transmission signals in consideration of the first transmission direction $Tx_1$ and the elements 311 based on the pulse repeat interval, as shown in FIG. 7. Thus, the ultrasound probe 310 may be configured to convert the first Doppler mode transmission signals provided from the transmitting section 320 into the ultrasound signals, transmit the ultrasound signals to living body in the first transmission direction $Tx_1$, and receive the ultrasound echo signals from the living body to output the first Doppler mode reception signals. The transmitting section 320 may be further configured to generate the second Doppler mode transmission signals in consideration of the second transmission direction $Tx_2$ and the elements 311 based on the pulse repeat interval, as shown in FIG. 7. Thus, the ultrasound probe 310 may be configured to convert the second Doppler mode transmission signals provided from the transmitting section 320 into the ultrasound signals, transmit the ultrasound signals to the living body in the second transmission direction $Tx_2$, and receive the ultrasound echo signals from the living body to output the second Doppler mode reception signals.

As described above, the transmitting section 320 may be configured to generate the first Doppler mode transmission signals and the second Doppler mode transmission signals corresponding to the ensemble number based on the pulse repeat interval.

Referring back to FIG. 3, the ultrasound data acquiring unit 120 may further include a receiving section 330. The receiving section 330 may be configured to perform an analog-digital conversion upon the reception signals provided from the ultrasound probe 310 to form sampling data. The receiving section 330 may be further configured to perform a reception beam-forming upon the sampling data in consideration of the elements 311 to form reception-focused data. The reception beam-forming will be described below in detail.

In one embodiment, the receiving section 330 may be configured to perform the analog-digital conversion upon the brightness mode reception signals provided from the ultrasound probe 310 to form sampling data (hereinafter referred to as "brightness mode sampling data"). The receiving section 330 may be further configured to perform the reception beam-forming upon the brightness mode sampling data to form reception-focused data (hereinafter referred to as "brightness mode reception-focused data").

The receiving section 330 may be further configured to perform the analog-digital conversion upon the Doppler mode reception signals provided from the ultrasound probe 310 to form sampling data (hereinafter referred to as "Doppler mode sampling data"). The receiving section 330 may be further configured to perform the reception beam-forming upon the Doppler mode sampling data to form reception-focused data (hereinafter referred to as "Doppler mode reception-focused data") corresponding to at least one reception direction of the ultrasound echo signals (i.e., reception beam).

As one example, the receiving section 330 may be configured to perform the analog-digital conversion upon the Doppler mode reception signals provided from the ultrasound probe 310 to form the Doppler mode sampling data. The receiving section 330 may be further configured to perform the reception beam-forming upon the Doppler mode sampling data to form first Doppler mode reception-focused data corresponding to a first reception direction $Rx_1$ and second Doppler mode reception-focused data corresponding to a second reception direction $Rx_2$, as shown in FIG. 4.

As another example, the receiving section 330 may be configured to perform the analog-digital conversion upon the first Doppler mode reception signals provided from the ultrasound probe 310 to form first Doppler mode sampling data corresponding to the first transmission direction $Tx_1$, as shown in FIG. 5. The receiving section 330 may be further configured to perform the reception beam-forming upon the first Doppler mode sampling data to form the first Doppler mode reception-focused data corresponding to the first reception direction $Rx_1$. The receiving section 330 may be also configured to perform the analog-digital conversion upon the second Doppler mode reception signals provided from the ultrasound probe 310 to form second Doppler mode sampling data corresponding to the second transmission direction $Tx_2$, as shown in FIG. 5. The receiving section 330 may be further configured to perform the reception beam-forming upon the second Doppler mode sampling data to form the second Doppler mode reception-focused data corresponding to the second reception direction $Rx_2$. If the reception direction is perpendicular to the elements 311 of the ultrasound probe 310, then a maximum aperture size may be used.

The reception beam-forming may be described with reference to the accompanying drawings.

In one embodiment, the receiving section 330 may be configured to perform the analog-digital conversion upon the reception signals provided through a plurality of channels $CH_k$, wherein $1 \leq k \leq N$, from the ultrasound probe 310 to form sampling data $S_{i,j}$, wherein the i and j are a positive integer, as shown in FIG. 8. The sampling data $S_{i,j}$ may be stored in a storage unit 140. The receiving section 330 may be further configured to detect pixels corresponding to the sampling data based on positions of the elements 311 and positions (orientation) of pixels of the ultrasound image UI with respect to the elements 311. That is, the receiving section 330 may select the pixels, which the respective sampling data are used as pixel data thereof, during the reception beam-forming based on the positions of the elements 311 and the orientation of the respective pixels of the ultrasound image UI with respect to the elements 311. The receiving section 330 may be configured to cumulatively assign the sampling data corresponding to the selected pixels as the pixel data.

Figure 9:
Figure 10:
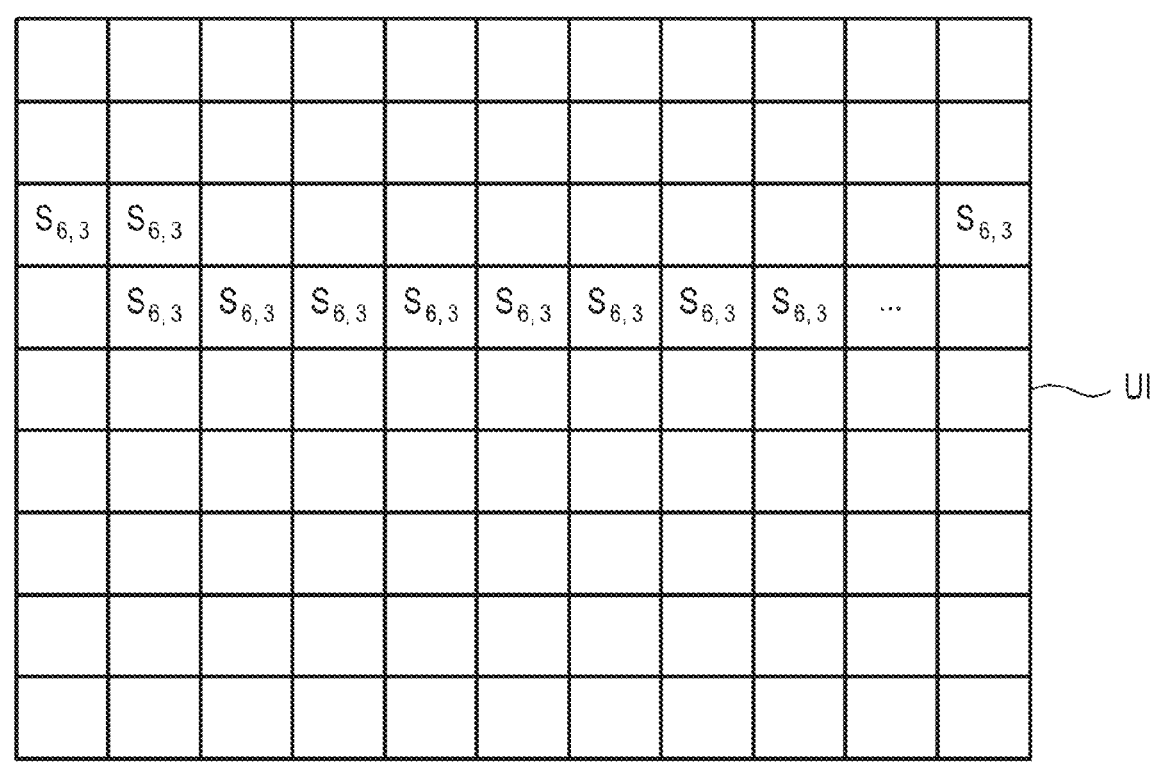

For example, the receiving section 330 may be configured to set a curve (hereinafter referred to as "reception beam-forming curve") $CV_{6,3}$ for selecting pixels, which the sampling data $S_{6,3}$ are used as the pixel data thereof, during the reception beam-forming based on the positions of the elements 311 and the orientation of the respective pixels of the ultrasound image UI with respect to the elements 311, as shown in FIG. 9. The receiving section 330 may be further configured to detect the pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, . . . $P_{3,N}$ corresponding to the reception beam-forming curve $CV_{6,3}$ from the pixels $P_{a,b}$ of the ultrasound image UI, wherein $1 \leq a \leq M$, $1 \leq b \leq N$. That is, the receiving section 330 may select the pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, . . . $P_{3,N}$ on which the reception beam-forming curve $CV_{6,3}$ passes among the pixels $P_{a,b}$ of the ultrasound image UI. The receiving section 330 may be also configured to assign the sampling data $S_{6,3}$ to the selected pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, . . . $P_{3,N}$, as shown in FIG. 10.

Figure 11:
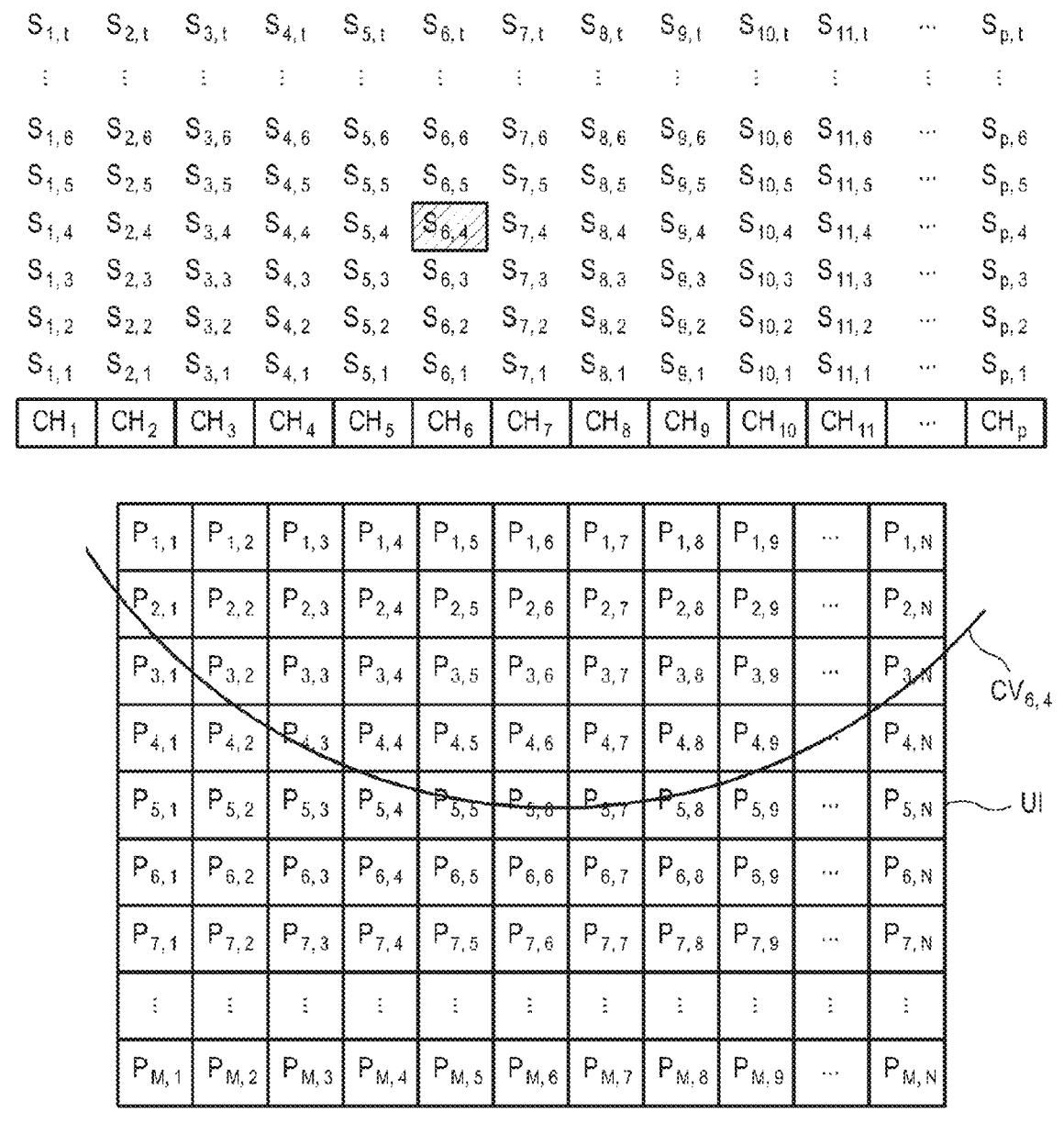
Figure 12:
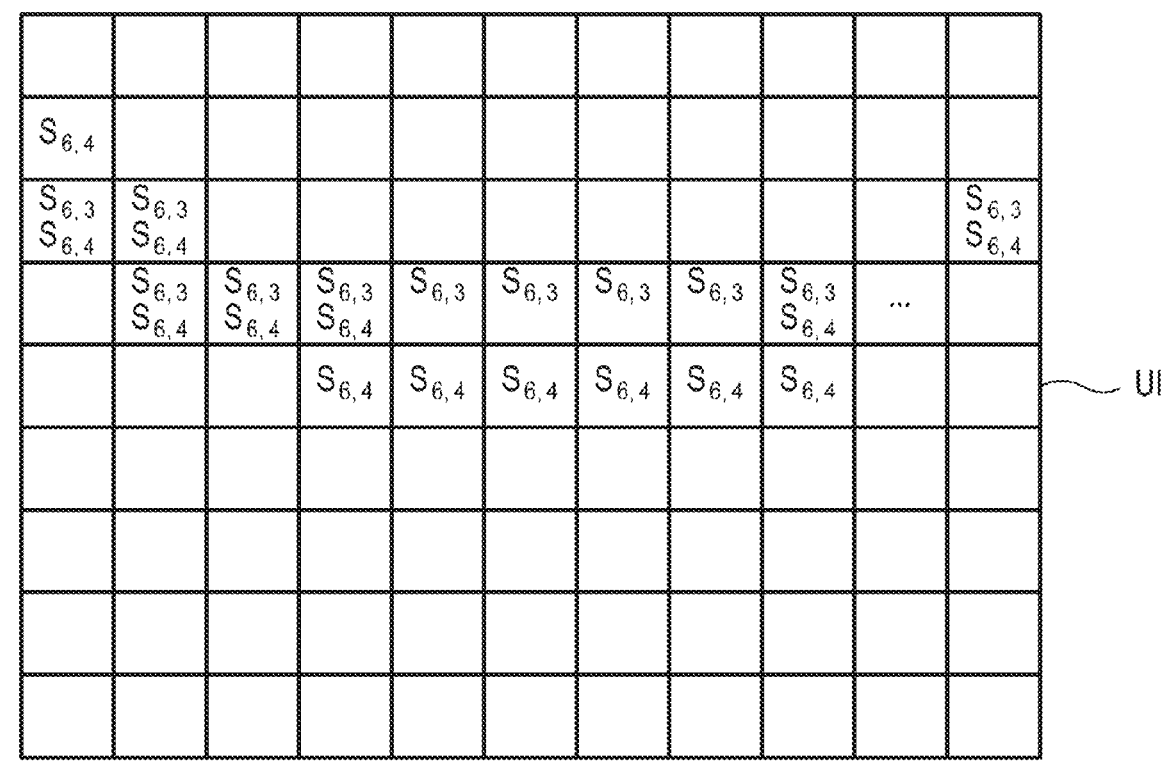

Thereafter, the receiving section 330 may be configured to set a reception beam-forming curve $CV_{6,4}$ for selecting pixels, which the sampling data $S_{6,4}$ are used as the pixel data thereof, during the reception beam-forming based on the positions of the elements 311 and the orientation of the respective pixels of the ultrasound image UI with respect to the elements 311, as shown in FIG. 11. The receiving section 330 may be further configured to detect the pixels $P_{2,1}$, $P_{3,1}$, $P_{3,2}$, $P_{4,2}$, $P_{4,3}$, $P_{4,4}$, $P_{5,4}$, $P_{5,5}$, $P_{5,6}$, $P_{5,7}$, $P_{5,8}$, $P_{4,9}$, $P_{5,9}$, . . . $P_{4,N}$, $P_{3,N}$ corresponding to the reception beam-forming curve $CV_{6,4}$ from the pixels $P_{a,b}$ of the ultrasound image UI. That is, the receiving section 330 may select the pixels $P_{2,1}$, $P_{3,1}$, $P_{3,2}$, $P_{4,2}$, $P_{4,3}$, $P_{4,4}$, $P_{5,4}$, $P_{5,5}$, $P_{5,6}$, $P_{5,7}$, $P_{5,8}$, $P_{4,9}$, $P_{5,9}$, . . . $P_{4,N}$, $P_{3,N}$ on which the reception beam-forming curve $CV_{6,4}$ passes among the pixels $P_{a,b}$ of the ultrasound image UI. The receiving section 330 may be additionally configured to assign the sampling data $S_{6,4}$ to the selected pixels $P_{2,1}$, $P_{3,1}$, $P_{3,2}$, $P_{4,2}$, $P_{4,3}$, $P_{4,4}$, $P_{5,4}$, $P_{5,5}$, $P_{5,6}$, $P_{5,7}$, $P_{5,8}$, $P_{4,9}$, $P_{5,9}$, . . . $P_{4,N}$, $P_{3,N}$, as shown in FIG. 12. In this way, the respective sampling data, which are used as the pixel data, may be cumulatively assigned to the pixels as the pixel data.

The receiving section 330 may be configured to perform the reception beam-forming (i.e., summing) upon the sampling data, which are cumulatively assigned to the respective pixels $P_{a,b}$ of the ultrasound image UI to form the reception-focused data.

In another embodiment, the receiving section 330 may be configured to perform the analog-digital conversion upon the reception signals provided through the plurality of channels $CH_k$ from the ultrasound probe 310 to form the sampling data $S_{i,j}$, as shown in FIG. 8. The sampling data $S_{i,j}$ may be stored in the storage unit 140. The receiving section 330 may be further configured to detect pixels corresponding to the sampling data based on the positions of the elements 311 and the positions (orientation) of the pixels of the ultrasound image UI with respect to the elements 311. That is, the receiving section 330 may select the pixels, which the respective sampling data are used as the pixel data thereof, during the reception beam-forming based on the positions of the elements 311 and the orientation of the respective pixels of the ultrasound image UI with respect to the elements 311. The receiving section 330 may be configured to cumulatively assign the sampling data corresponding to the selected pixels as the pixel data. The receiving section 330 may be further configured to determine pixels existing in the same column among the selected pixels. The receiving section 330 may be also configured to set weights corresponding to the respective determined pixels. The receiving section 330 may be additionally configured to apply the weights to the sampling data of the respective pixels.

For example, the receiving section 330 may be configured to set the reception beam-forming curve $CV_{6,3}$ for selecting pixels, which the sampling data $S_{6,3}$ are used as the pixel data thereof, during the reception beam-forming based on the positions of the elements 311 and the orientation of the respective pixels of the ultrasound image UI with respect to the elements 311, as shown in FIG. 9. The receiving section 330 may be further configured to detect the pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, . . . $P_{3,N}$ corresponding to the reception beam-forming curve $CV_{6,3}$ from the pixels $P_{a,b}$ of the ultrasound image UI, wherein $1 \leq a \leq M$, $1 \leq b \leq N$. That is, the receiving section 330 may select the pixels $P_{3,1}$, $P_{3,2}$ $P_{4,2}$, $P_{4,3}$, $P_{4,4}$, $P_{4,5}$, $P_{4,6}$, $P_{4,7}$, $P_{4,8}$, $P_{4,6}$, . . . $P_{3,N}$ on which the reception beam-forming curve $CV_{6,3}$ passes among the pixels $P_{a,b}$ of the ultrasound image UI. The receiving section 330 may be also configured to assign the sampling data $S_{6,3}$ to the selected pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, . . . $P_{3,N}$ as shown in FIG. 10. The receiving section 330 may be further configured to determine pixels $P_{3,2}$ and $P_{4,2}$, which exist in the same column among the selected pixels $P_{3,1}$, $P_{3,2}$, $P_{4,2}$, $P_{4,3}$, $P_{4,4}$, $P_{4,5}$, $P_{4,6}$, $P_{4,7}$, $P_{4,8}$, $P_{4,9}$, . . . $P_{3,N}$. The receiving section 330 may be further configured to calculate a distance $W_1$ from a center of the determined pixel $P_{3,2}$ to the reception beam-forming curve $CV_{6,3}$ and a distance $W_2$ from a center of the determined pixel $P_{4,2}$ to the reception beam-forming curve $CV_{6,3}$, as shown in FIG. 13. The receiving section 330 may be additionally configured to set a first weight $\alpha_1$ corresponding to the pixel $P_{3,2}$ based on the distance $W_1$ and a second weight $\alpha_2$ corresponding to the pixel $P_{4,2}$ based on the distance $W_2$. The first weight $\alpha_1$ and the second weight $\alpha_2$ may be set to be in proportional to or in inverse proportional to the calculated distances. The receiving section 330 may be further configured to apply the first weight $\alpha_1$ to the sampling data $S_{6,3}$ assigned to the pixel $P_{3,2}$ and to apply the second weight $\alpha_2$ to the sampling data $S_{6,3}$ assigned to the pixel $P_{4,2}$. The receiving section 330 may be configured to perform the above process upon the remaining sampling data.

The receiving section 330 may be configured to perform the reception beam-forming upon the sampling data, which are cumulatively assigned to the respective pixels $P_{a,b}$ of the ultrasound image UI to form the reception-focused data.

In yet another embodiment, the receiving section 330 may be configured to perform the analog-digital conversion upon the reception signals provided through the plurality of channels $CH_k$ from the ultrasound probe 310 to form the sampling data $S_{i,j}$, as shown in FIG. 8. The sampling data $S_{i,j}$ may be stored in the storage unit 140. The receiving section 330 may be further configured to set a sampling data set based on the sampling data $S_{i,j}$. That is, the receiving section 330 may set the sampling data set for selecting pixels, which the sampling data $S_{i,j}$ are used as the pixel data thereof, during the reception beam-forming.

Figure 14:
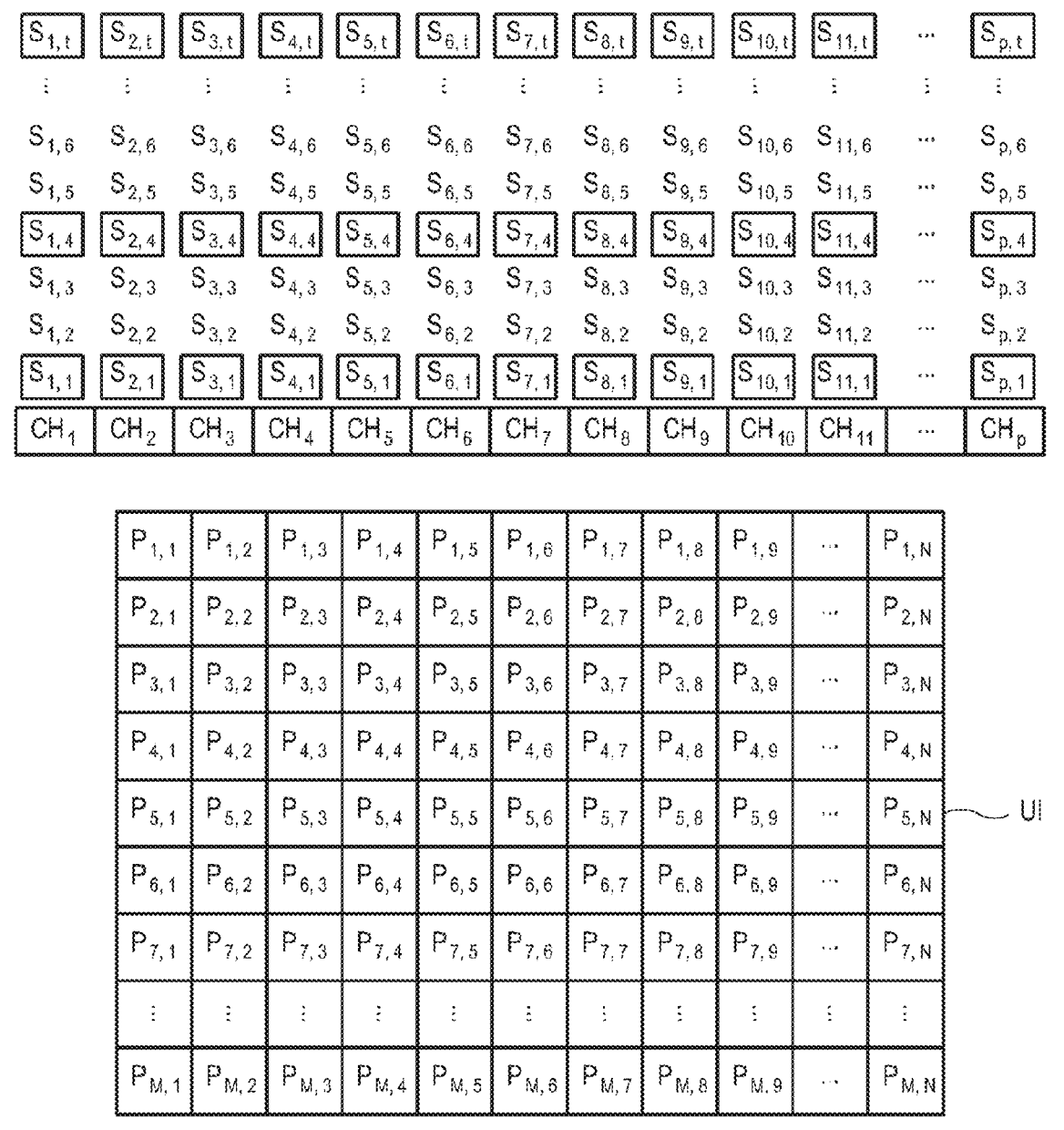

For example, the receiving section 330 may be configured to set the sampling data $S_{1,1}$, $S_{1,4}$, . . . $S_{1,t}$, $S_{2,1}$, $S_{2,4}$, $S_{2,t}$, $S_{p,t}$ as the sampling data set (denoted by a box) for selecting the pixels, which the sampling data $S_{i,j}$ are used as the pixel data thereof, during the reception beam-forming, as shown in FIG. 14.

The receiving section 330 may be further configured to detect the pixels corresponding to the respective sampling data of the sampling data set based on the positions of the elements 311 and the positions (orientation) of the respective pixels of the ultrasound image UI with respect to the elements 311. That is, the receiving section 330 may select the pixels, which the respective sampling data of the sampling data set are used as the pixel data thereof, during the reception beam-forming based on the positions of the elements 311 and the orientation of the respective pixels of the ultrasound image UI with respect to the elements 311. The receiving section 330 may be further configured to cumulatively assign the sampling data to the selected pixels in the same manner as the above embodiments. The receiving section 330 may be also configured to perform the reception beam-forming upon the sampling data, which are cumulatively assigned to the respective pixels of the ultrasound image UI to form the reception-focused data.

In yet another embodiment, the receiving section 330 may be configured to perform down-sampling upon the reception signals provided through the plurality of channels $CH_k$ from the ultrasound probe 310 to form down-sampled data. As described above, the receiving section 330 may be further configured to detect the pixels corresponding to the respective sampling data based on the positions of the elements 311 and the positions (orientation) of the respective pixels of the ultrasound image UI with respect to the elements 311. That is, the receiving section 330 may select the pixels, which the respective sampling data are used as the pixel data thereof, during the reception beam-forming based on the positions of the elements 311 and the orientation of the pixels of the ultrasound image UI with respect to the elements 311. The receiving section 330 may be further configured to cumulatively assign the respective sampling data to the selected pixels in the same manner as the above embodiments. The receiving section 330 may be further configured to perform the reception beam-forming upon the sampling data, which are cumulatively assigned to the respective pixels of the ultrasound image UI to form the reception-focused data.

However, it should be noted herein that the reception beam-forming may not be limited thereto.

Referring back to FIG. 3, the ultrasound data acquiring unit 120 may further include an ultrasound data forming section 340. The ultrasound data forming section 340 may be configured to form the ultrasound data corresponding to the ultrasound image based on the reception-focused data provided from the receiving section 330. The ultrasound data forming section 340 may be further configured to perform a signal process (e.g., gain control, etc) upon the reception-focused data.

In one embodiment, the ultrasound data forming section 340 may be configured to form ultrasound data (hereinafter referred to as "brightness mode ultrasound data") corresponding to the brightness mode image based on the brightness mode reception-focused data provided from the receiving section 330. The brightness mode ultrasound data may include radio frequency data.

The ultrasound data forming section 340 may be further configured to form ultrasound data (hereinafter referred to as "Doppler mode ultrasound data") corresponding to the first region of interest $ROI_1$ based on the Doppler mode reception-focused data provided from the receiving section 330. The Doppler mode ultrasound data may include in-phase/ quadrature data. However, it should be noted herein that the Doppler mode ultrasound data may not be limited thereto.

For example, the ultrasound data forming section 340 may form first Doppler mode ultrasound data based on the first Doppler mode reception-focused data provided from the receiving section 330. The ultrasound data forming section 340 may further form second Doppler mode ultrasound data based on the second Doppler mode reception-focused data provided from the receiving section 330.

Referring back to FIG. 1, the ultrasound system 100 may further include a processing unit 130 in communication with the user input unit 110 and the ultrasound data acquiring unit 120. The processing unit 130 may include a central processing unit, a microprocessor, a graphic processing unit and the like.

Figure 15:
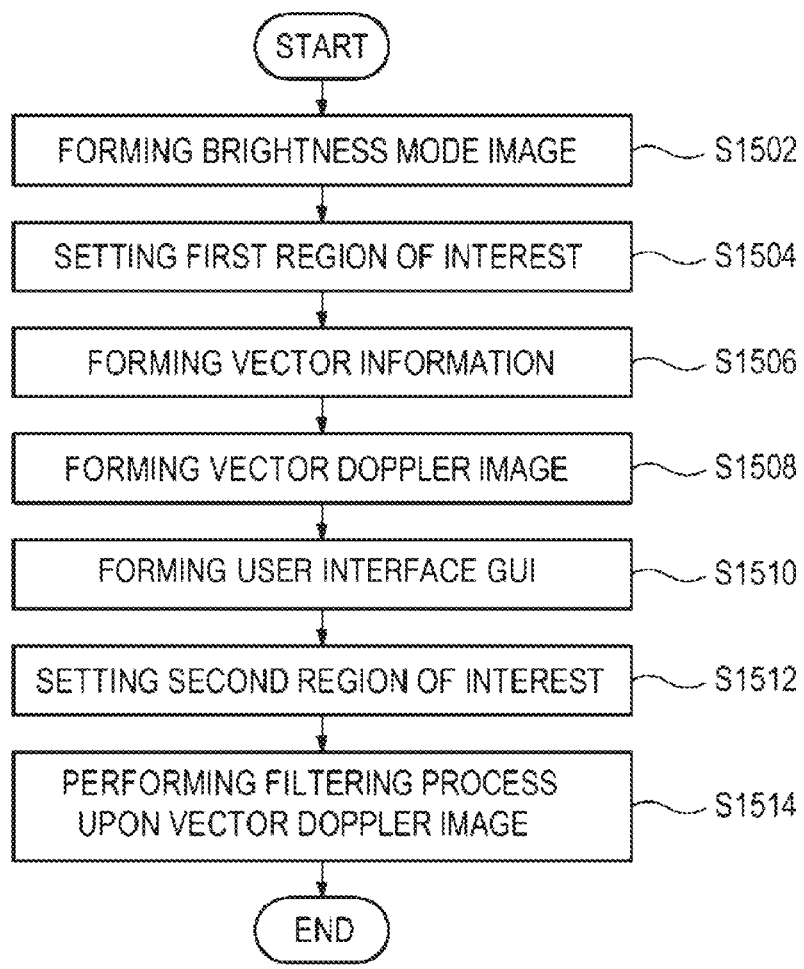
FIG. 15 is a flow chart showing a process of providing a user interface for a filtering process upon a vector Doppler image.

FIG. 15 is a flow chart showing a process of providing the user interface. The processing unit 130 may be configured to form the brightness mode image BI based on the brightness mode ultrasound data provided from the ultrasound data acquiring unit 120, at step S1502 in FIG. 15. The brightness mode image BI may be displayed on a display unit 150.

The processing unit 130 may be configured to set the first region of interest ROI$_1$ on the brightness mode image BI based on the input information (i.e., first input information) provided from the user input unit 110, at step S1504 in FIG. 15. Thus, the ultrasound data acquiring unit 120 may be configured to transmit the ultrasound signals to the living body and receive the ultrasound echo signals from the living body to acquire the Doppler mode ultrasound data corresponding to the first region of interest ROI$_1$.

The processing unit 130 may be configured to form vector information based on the Doppler mode ultrasound data provided from the ultrasound data acquiring unit 120, at step S1506 in FIG. 15. That is, the processing unit 130 may form the vector information corresponding to the motion (i.e., velocity and direction) of the target object based on the Doppler mode ultrasound data.

Generally, when the transmission direction of the ultrasound signals is equal to the reception direction of the ultrasound echo signals and a Doppler angle is 0, the following relationship may be established:

$$X \cos \theta = \frac{C_0 f_d}{2 f_0} \tag{1}$$

In equation 1, X represents a reflector velocity (i.e., velocity of target object), $C_0$ represents a sound speed in the living body, $f_d$ represents a Doppler shift frequency, and $f_0$ represents an ultrasound frequency.

The Doppler shift frequency $f_d$ may be calculated by the difference between a frequency of the ultrasound signals (i.e., transmission beam) and a frequency of the ultrasound echo signals (i.e., reception beam). Also, the velocity component $X \cos \theta$ projected to the transmission direction may be calculated by equation 1.

When the transmission direction of the ultrasound signals (i.e., transmission beam) is different from the reception direction of the ultrasound echo signals (i.e., reception beam), the following relationship may be established:

$$X \cos \theta_T + X \cos \theta_R = \frac{C_0 f_d}{f_0} \tag{2}$$

In equation 2, $\theta_T$ represents an angle between the ultrasound signals (i.e., transmission beam) and the blood flow, and $\theta_R$ represents an angle between the ultrasound echo signals (i.e., reception beam) and the blood flow.

FIG. 16 is a schematic diagram showing an example of the transmission directions, the reception directions, the vector information and an over-determined problem. Referring to FIG. 16, when the ultrasound signals (i.e., transmission beam) are transmitted in a first direction D1 and the ultrasound echo signals (i.e., reception beam) are received in the first direction D1, the following relationship may be established:

$$\vec{\alpha}_1 \vec{X} = \alpha_{11} x_1 + \alpha_{12} x_2 = y_1 = X \cos \theta \tag{3}$$

In equation 3, $\vec{\alpha}_1 = (\alpha_{11}, \alpha_{12})$ represents a unit vector of the first direction D1, $\vec{X} = (x_1, x_2)$ represents variables, and $y_1$ is calculated by equation 1.

When the ultrasound signals (i.e., transmission beam) are transmitted in a second direction D2 and the ultrasound echo signals (i.e., reception beam) are received in a third direction D3, the following relationship may be established:

$$(\alpha_{21} + \alpha_{31}) x_1 + (\alpha_{22} + \alpha_{32}) x_2 = (y_2 + y_3) = X \cos \theta_2 + X \cos \theta_3 \tag{4}$$

Equations 3 and 4 assume a two-dimensional environment. However, equations 3 and 4 may be expanded to a three-dimensional environment. That is, when expanding equations 3 and 4 to the three-dimensional environment, the following relationship may be established:

$$\alpha_{11} x_1 + \alpha_{12} x_2 + \alpha_{13} x_3 = y \tag{5}$$

In the case of the two-dimensional environment (i.e., two-dimensional vector), at least two equations are required to calculate the variables $x_1$ and $x_2$. For example, when the ultrasound signals (i.e., transmission beam) are transmitted in the third direction D3 and the ultrasound echo signals (i.e., reception beam) are received in the second direction D2 and a fourth direction D4 as shown in FIG. 16, the following equations may be established:

$$(\alpha_{31} + \alpha_{21}) x_1 + (\alpha_{32} + \alpha_{22}) x_2 = (y_3 + y_2)$$

$$(\alpha_{31} + \alpha_{41}) x_1 + (\alpha_{32} + \alpha_{42}) x_2 = (y_3 + y_4) \tag{6}$$

The vector $\vec{X} = (x_1, x_2)$ may be calculated by the equations of equation 6.

When the reception beam-forming is performed in at least two angles (i.e., at least two reception directions), at least two equations may be obtained and represented as the over-determined problem, as shown in FIG. 16. The over-determined problem is well known in the art. Thus, it has not been described in detail so as not to unnecessarily obscure the present disclosure. The over-determined problem may be solved by a pseudo inverse method, a weighted least square method and the like based on noise characteristics added to the Doppler shift frequency. That is, M×N equations may be obtained by M transmission directions and the reception beam-forming of N reception directions at every transmission.

Figure 17:
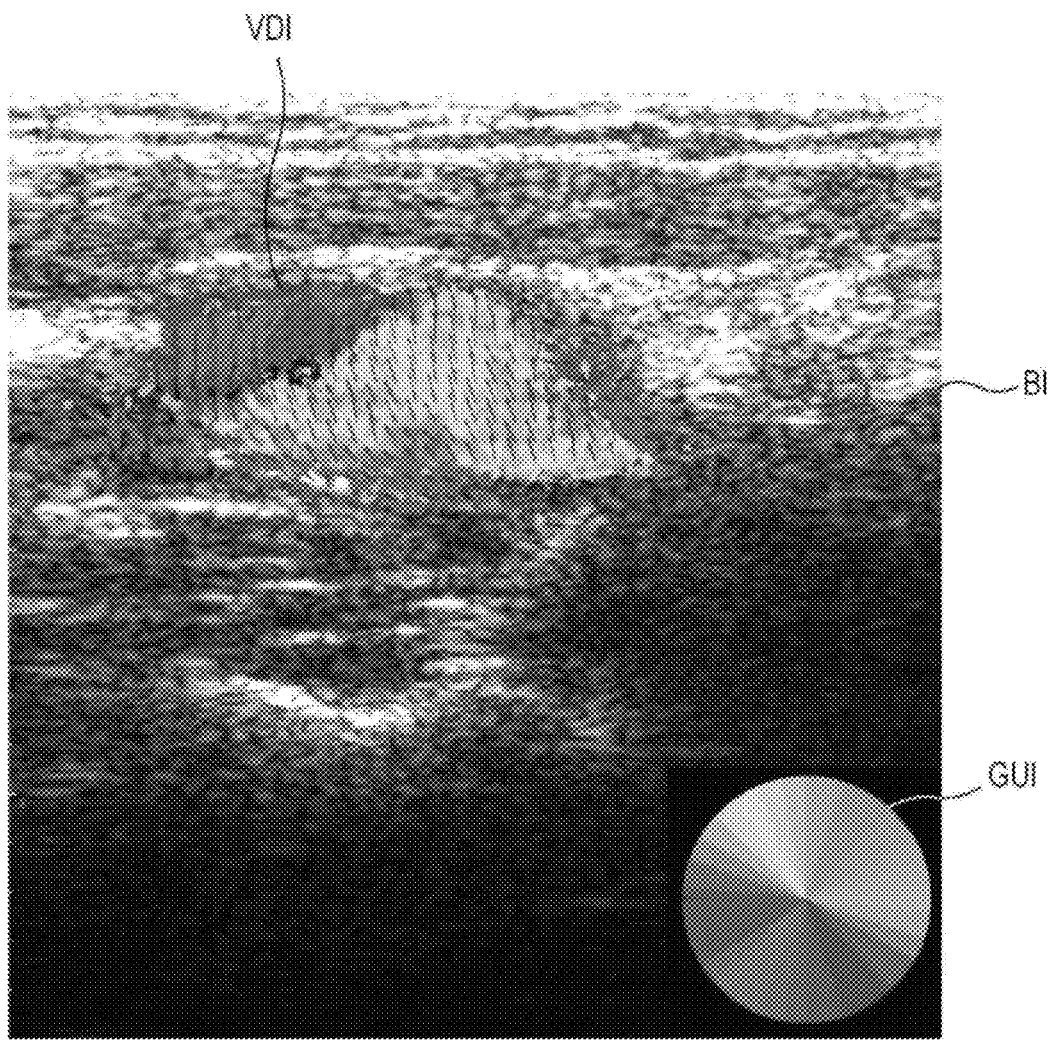
FIG. 17 is a schematic diagram showing an example of the brightness mode image, the vector Doppler image and the user interface.

The processing unit 130 may be configured to form a vector Doppler image VDI as shown in FIG. 17 based on the vector information, at step S1508 in FIG. 15. The methods of forming the vector Doppler image VDI are well known in the art. Thus, they have not been described in detail so as not to unnecessarily obscure the present disclosure.

Optionally, the processing unit 130 may be configured to compound the brightness mode image BI and the vector Doppler image VDI to form a compound image.

The processing unit 130 may be configured to form the user interface GUI as shown in FIG. 17 based on the vector information, at step S1510 in FIG. 15. The user interface GUI may be an interface mapping the vector information corresponding to the motion (i.e., velocity and direction) of the target object to colors. That is, the user interface GUI may be an interface for performing a filtering process upon the vector Doppler image VDI. The user interface GUI may be displayed on the display unit 150.

In operation S1512, the processing unit 130 may determine a second region of interest in the user interface GUI, based on input information (i.e., second input information).

Figure 18:
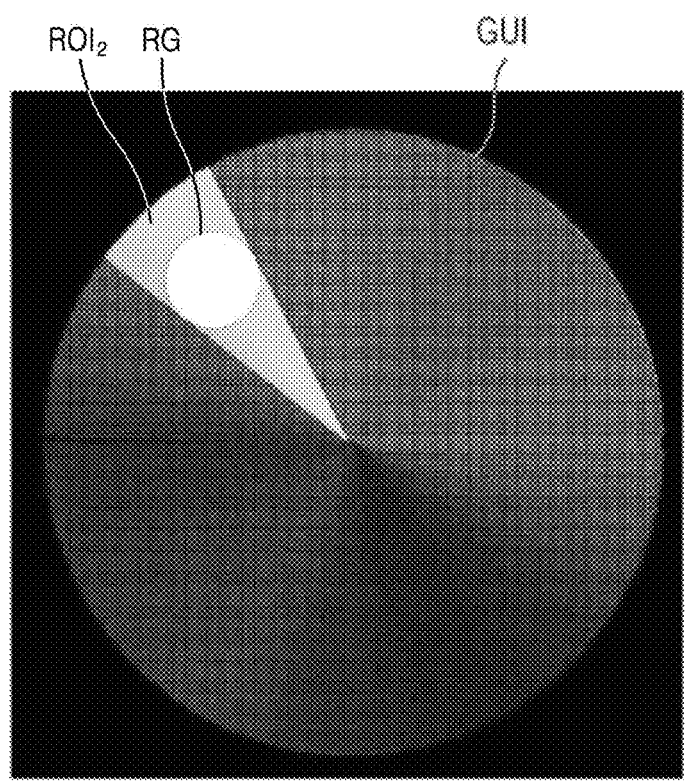
FIGS. 18 to 20 are schematic diagrams showing an example of the user interface.
Figure 19:
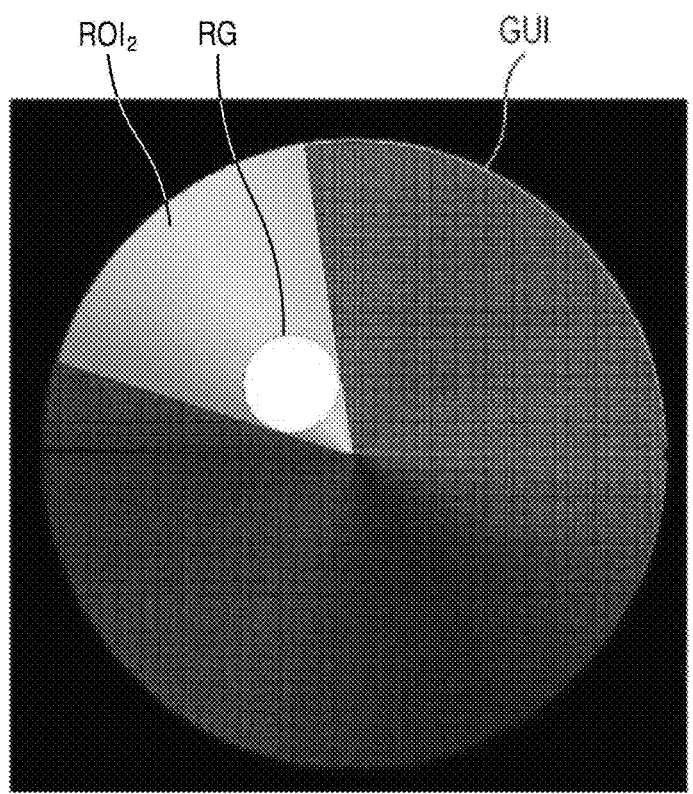

As an example, as shown in FIGS. 18 and 19, if second input information for touching a region RG on the user interface GUI, the touching being performed by a user, is received from the user input unit 110, the processing unit 130 may determine a second region of interest ROI$_2$, which includes the region RG corresponding to the second input information, with reference to a center of the user interface GUI.

Figure 20:
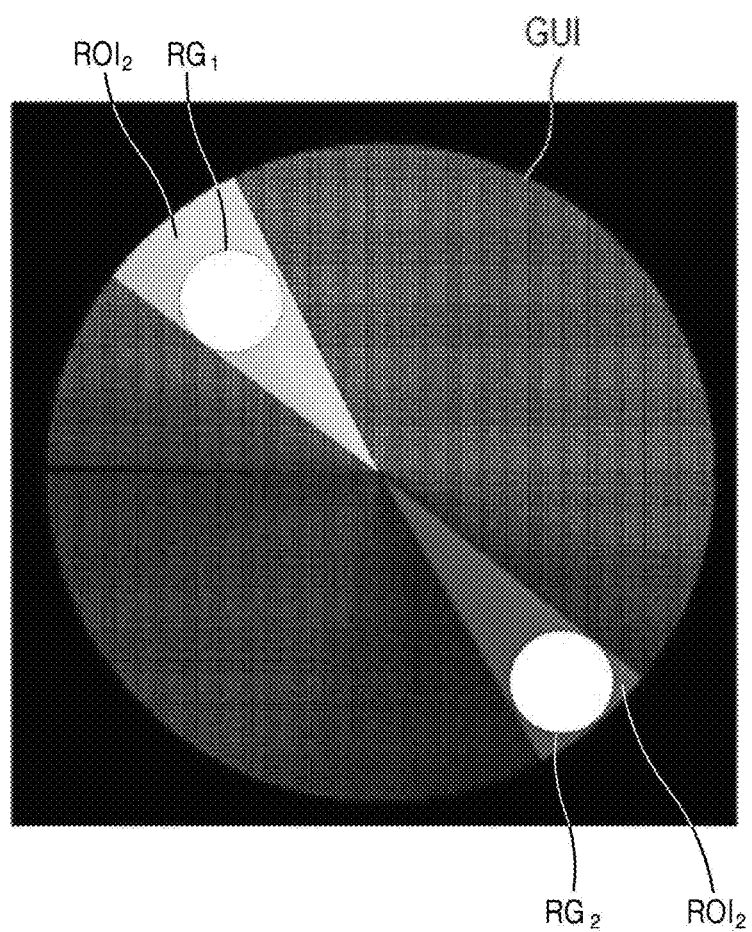

As another example, as shown in FIG. 20, if the second input information for touching two regions $RG_1$ and $RG_2$ on the user interface GUI, the touching being performed by the user, is received from the user input unit 110, the processing unit 130 may determine a second region of interest $ROI_2$, which includes the two regions $RG_1$ and $RG_2$ corresponding to the second input information, with reference to the center of the user interface GUI.

The processing unit 130 may be configured to perform a filtering process upon the vector Doppler image VDI based on the second region of interest $ROI_2$, at step S1514 in FIG. 15. In one embodiment, the processing unit 130 may be configured to perform the filtering process for representing only the vector information (i.e., velocity and direction of the target object) corresponding to the second region of interest $ROI_2$ upon the vector Doppler image VDI. That is, the processing unit 130 may perform the filtering process for not representing the vector information not corresponding to the second region of interest $ROI_2$ upon the vector Doppler image VDI.

In the above embodiment, the filtering process for representing only the vector information corresponding to the second region of interest $ROI_2$ is performed upon the vector Doppler image VDI. However, it should be noted herein that the filtering process may not be limited thereto.

Referring back to FIG. 1, the ultrasound system 100 may further include the storage unit 140. The storage unit 140 may store the ultrasound data (i.e., brightness mode ultrasound data and Doppler mode ultrasound data) acquired by the ultrasound data acquiring unit 120. The storage unit 140 may additionally store the vector information formed by the processing unit 130.

The ultrasound system 100 may further include the display unit 150. The display unit 150 may be configured to display the brightness mode image BI formed by the processing unit 130. The display unit 150 may be also configured to display the vector Doppler image VDI formed by the processing unit 130. The display unit 150 may be additionally configured to display the user interface GUI formed by the processing unit 130.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound image processing apparatus comprising:
a display configured to display a first user interface, wherein the first user interface comprises a first region corresponding to a vector Doppler image, and a second region corresponding to a graphic user interface for receiving a selection of vector information of a motion of an object, wherein the graphic user interface is circular and of a touch type;
an input device comprising a touch screen, and configured to receive a first touch input to select a first region of interest in the first region and to receive second touch inputs in the circular graphic user interface to respectively select sector regions of the circular graphic user interface as second regions of interest within the graphic user interface; and
a processor configured to:
form vector information of the motion of the object corresponding to the first region of interest based on Doppler mode ultrasound data, wherein the vector information includes a direction and a velocity of the motion of the object,
when one of the second touch inputs in the graphic user interface has a first distance to a center of the circular graphic user interface, determine a first center angle of one of the sector regions selected by the one of the second touch inputs, perform a first filtering process upon the vector Doppler image so as to filter out unselected vector information other than vector information, corresponding to the one of the sector regions having the first center angle as one of the second regions of interest, from among the formed vector information, and update the vector Doppler image based on the result of the first filtering process, and
when another of the second touch inputs in the graphic user interface having a second distance to the center of the circular graphic user interface is less than the first distance, determine a second center angle of another of the sector regions selected by the another of the second touch inputs to be greater than the first center angle, perform a second filtering process upon the vector Doppler image so as to filter out unselected vector information other than vector information, corresponding to the another of the sector regions having the second center angle as another of the second regions of interest, from among the formed vector information, and update the vector Doppler image based on the result of the second filtering process.

2. The ultrasound image processing apparatus of claim 1, wherein the second region maps the vector information to colors.

3. The ultrasound image processing apparatus of claim 1, wherein the input device is configured to receive the first input which selects a plurality of first regions of interest within the vector Doppler image.

4. The ultrasound image processing apparatus of claim 1, wherein the processor is configured to display the vector information corresponding to a selected one of the second regions of interest on the vector Doppler image by using at least one arrow and at least one color.

5. The ultrasound image processing apparatus of claim 1, wherein the second region comprises a plurality of regions having colors, and the colors in the plurality of regions correspond to the vector information of the motion of the object.

6. A method of processing an ultrasound image, comprising:
displaying a first user interface, wherein the first user interface comprises a first region corresponding to a vector Doppler image, and a second region corresponding to a graphic user interface for receiving a selection of vector information of a motion of an object, wherein the graphic user interface is circular and of a touch type;
receiving a first touch input to select a first region of interest in the first region and second touch inputs in the circular graphic user interface to respectively select sector regions of the circular graphic user interface as second regions of interest within the graphic user interface;

forming vector information of the motion of the object corresponding to the first region of interest based on Doppler mode ultrasound data, wherein the vector information includes a direction and a velocity of the motion of the object;

when one of the second touch inputs in the graphic user interface has a first distance to a center of the circular graphic user interface, determining a first center angle of one of the sector regions selected by the one of the second touch inputs, performing a first filtering process upon the vector Doppler image so as to filter out unselected vector information other than vector information, corresponding to the one of the sector regions having the first center angle as one of the second regions of interest, from among the formed vector information and updating the vector Doppler image based on the result of the first filtering process; and when another of the second touch inputs in the graphic user interface having a second distance to the center of the circular graphic user interface is less than the first distance, determining a second center angle of another of the sector regions selected by the another of the second touch inputs to be greater than the first center angle, performing a second filtering process upon the vector Doppler image so as to filter out unselected vector information other than vector information, corresponding to the another of the sector regions having the second center angle as another of the second regions of interest, from among the formed vector information, and updating the vector Doppler image based on the result of the second filtering process.

7. The method of claim 6, wherein the second region maps the vector information to colors.

8. The method of claim 6, wherein the receiving the first input comprises receiving the first input which selects a plurality of first regions of interest within the vector Doppler image.

9. The method of claim 6, wherein the updating the vector Doppler image comprises displaying the vector information corresponding to a selected one of the second regions of interest on the vector Doppler image by using at least one arrow and at least one color.

10. The method of claim 6, wherein the second region comprises a plurality of regions having colors, and the colors in the plurality of regions correspond to the vector information of the motion of the object.

* * * * *